United States Patent [19]

Schmukler et al.

[11] Patent Number: 4,710,643

[45] Date of Patent: Dec. 1, 1987

[54] METHOD AND APPARATUS FOR DETERMINING THE DEGREE OF PURITY OF A LIQUID

[75] Inventors: Charles S. Schmukler, Flushing; Georges A. Buon, Whitestone, both of N.Y.

[73] Assignee: Marine Moisture Control Company, Inc., Inwood, N.Y.

[21] Appl. No.: 894,956

[22] Filed: Aug. 8, 1986

[51] Int. Cl.$^4$ ............................................. G01N 15/06
[52] U.S. Cl. ................................... 250/573; 250/575; 356/435; 356/442
[58] Field of Search ............... 250/573, 575, 564, 574, 250/576; 356/435, 436, 440, 442; 73/53

[56] References Cited

U.S. PATENT DOCUMENTS 3,854,878  12/1974  Kiesow .............................. 356/436
3,954,342  5/1976   Boeke .............................. 250/575
4,099,882  7/1978   Andrén et al. ..................... 250/575
4,110,044  8/1978   Pettersson et al. ................ 250/564
4,468,124  8/1984   Berick ............................. 356/435

Primary Examiner—Edward P. Westin
Assistant Examiner—Charles Wieland
Attorney, Agent, or Firm—McAulay, Fields, Fisher, Goldstein & Nissen

[57] ABSTRACT

Method and apparatus for monitoring the purity of a liquid in a container by passing a laser beam divided into two portions with the first portion passing through a pair of quartz windows with the liquid in a container therebetween, and the second portion being directed through the two windows and the liquid, the first portion being detected to detect the amount of solid particles in the liquid, and the second portion being detected to determine changes in refraction index to obtain a recording of the purity of the liquid.

18 Claims, 1 Drawing Figure

METHOD AND APPARATUS FOR DETERMINING THE DEGREE OF PURITY OF A LIQUID

BACKGROUND OF THE INVENTION

This invention is concerned with a method and apparatus for determining the degree of purity of a liquid and, ancilliary thereto, to control the purity of a liquid.

In industrial processes, the degree of purity of liquids, or the similarity of a liquid to a reference liquid may have to be determined with great accuracy. Moreover, it may also be necessary to maintain the characteristics of liquids similar to each other so that they are almost the same.

It is well known that the purity of a liquid may be altered during the transfer of the liquid from one receptacle to another, such as pouring the liquid from one receptacle into another, during a processing phase of the liquid, or the use of a liquid as a component of a working medium, such as water in turbo-machinery, which will change the purity of the liquid. Also, the purity of a liquid may change at different times during storage.

The purity of a normally transparent liquid can be altered either by solid particles in suspension or by a dissolution of various chemicals.

SUMMARY OF THE INVENTION

It is proposed to provide an apparatus to monitor the purity of liquid. Such liquid may be continuously or intermittently monitored in order to detect any variation or alteration in the purity.

It is also proposed to provide a method for detecting variations or an alteration in liquid purity.

For this purpose, it is proposed to use known properties of light beams as they pass through liquids. The apparatus generally includes a pair of quartz windows placed at diametrically opposite sides of a liquid, the purity of which is to be monitored. A light is passed through the liquid, and the change in characteristics thereof is measured. A laser light beam is the preferred light source.

In carrying out the invention, it is preferred to use a light source of controlled energy, monochromatic or coherent at a wavelength which is in the blue-green portion of the spectrum having a wavelength of approximately 0.488 microns which is the wavelength at which silicon photo-detectors operate with maximum efficiency.

The wavelength of the light source is preferably in the range between 0.439 and 0.537 microns for suitable and optimum operation.

The laser light beam is first divided into two portions by an appropriate conventional beam splitter and directed in two different directions.

The first portion of the beam is impinged onto a beam expander and enters and exits the beam expander in order to survey a relatively large liquid area or cross-section of the liquid passing between the quartz windows. A large area silicon photo-cell is placed proximate to the exit from the second window and energized by the light impinging thereon. Any amount of solid particles or other suspension present in the liquid will be detected by diminishing of energy. With appropriate instrumentation connected with the photo-cell, it is possible to trigger the kind of actions necessary with this liquid. This first portion can form an optical train and is a particles detector.

The second portion of the beam exits from the beam splitter from the first portion by being diverted towards a laser beam retractor and then towards a mirror arrangement. The laser beam retractor is used so as to make the second beam as small as possible, e.g. 1 mm in diameter. Like the first beam section, the second beam will enter one of the windows, pass through the liquid and exit from the other window after having passed through the liquid and the two windows. At the exit, a second detector is provided which will receive energy resulting from the second beam after passing through two collimating pin holes before reaching the second detector.

The second portion of the beam will exit from the two windows at an angle due to the refractive index of the liquid. It will then enter a set of pin holes to reach a photo cell at the end of an enclosure. If the chemical nature of the liquid is changed, from whatever cause, the index of refraction is changed and consequently will not reach the photo cell, thereby insuring immediate detection.

While the preferred embodiment of the invention proposes to place the windows diametrically opposite to each other, it is within the scope of the invention to use two spaced windows placed in such a manner that the laser light beams pass through the liquid being monitored.

To control a liquid purity, or its similarity to a reference sample, the apparatus can be arranged to monitor intermittently or continuously any alteration in the liquid.

The apparatus uses the properties of light beams passing through the liquid as it passes between a set of windows.

When the purity is correct, the first photo-cell will be responsive to the first portion and is energized so that the signal is recognized. When and if any chemical dissolution or change occurs in the liquid, transmitivity may or may not be detected by the first beam responsive photo-cell. However, the second portion beam is affected by a deviation of its path due to the refraction index of the altered liquid that is different from the liquid when it was in its pure state.

A conduit with collimating pin-holes in transverse walls is provided proximate to the exit of the second portion and controls the angle of the light directed to the refraction sensing photo-cell. This information through processing will allow taking proper action.

This second beam portion of the system can also be designated a foreign chemical dissolution detector.

Such system is valid for any transparent liquid such as water, hydrocarbons, alcohols, ketones, etc.

BRIEF DESCRIPTION OF THE DRAWING

The single FIGURE of the drawing illustrates the system and apparatus for carrying out the invention and practicing the invention.

DETAILED DESCRIPTION OF THE INVENTION

Figure 1:
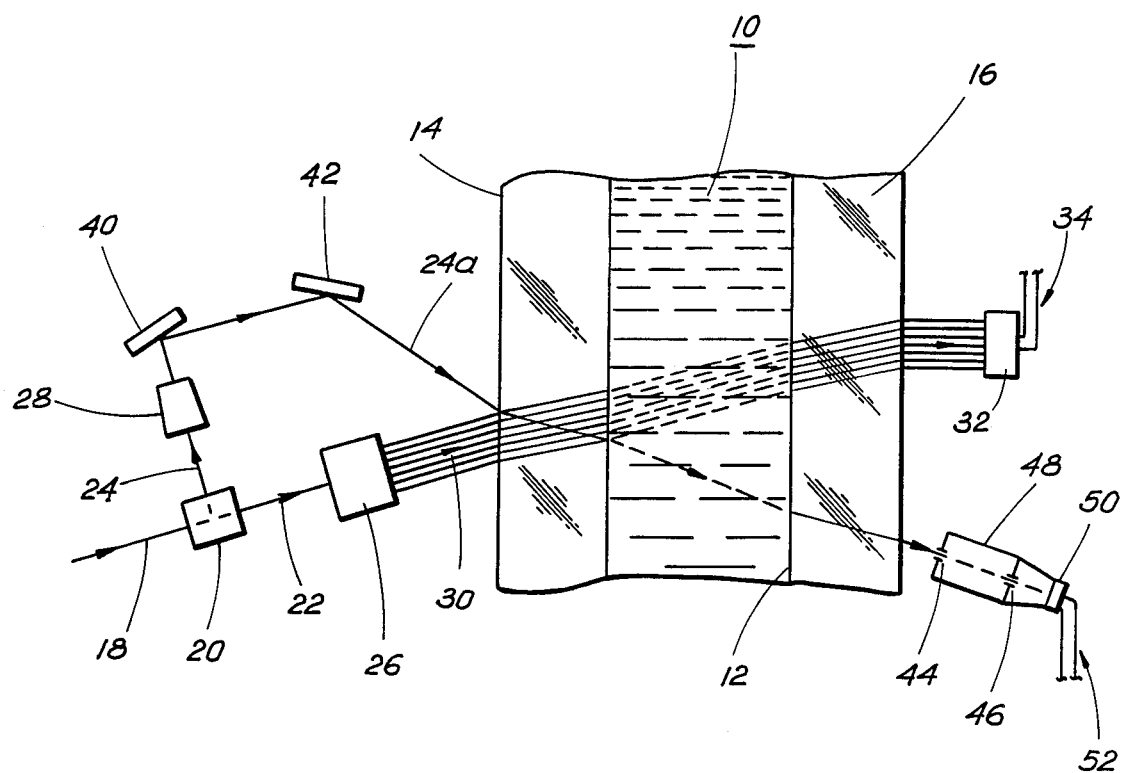

Referring now to the single FIGURE of the drawing, and which illustrates the best mode presently contemplated by me for carrying out the invention, a liquid 10 in a portion of a conduit 12 shown in section is transparent to laser energy and is passing between two diametrically opposed windows 14, 16.

A laser beam 18 provided by a conventional source, not shown, is directed to a semi-transparent beam splitter 20 to split the laser beam into first and second portions 22 and 24. First portion 22 is directed to a beam expander 26, and second portion 24 is directed towards a beam retractor 28.

Beam expander 26 is aligned with the beam splitter to receive the first portion 22.

Beam expander 26 widens or expands the width of the beam in a direction perpendicular to the direction of beam travel to survey or encompass a large area or cross-section of the liquid 10 passing or flowing through conduit 12. Flow of liquid 10 in conduit 12 is slow and may be considered equivalent to laminar flow. First portion 22 of the beam is expanded as at 30 by beam expander 26 and enters conduit 12 through window 14, passes through liquid 10 and exits through window 16 and impinges onto a large photo-cell 32 which is connected to circuits 34 coupled to a recorder (not shown) to record the quantity or density of particles in liquid 10. Other equipment not forming part of this invention can be used to take whatever action is necessary based on the particles in the liquid.

The second portion 24 is directed through beam retractor or condenser 28 towards a pair of angularly related mirrors 40, 42 to direct the second portion 24a after having its direction changed by the mirrors for impingement onto the first window 14 to pass through liquid 10 and exit from the second window 16. Because the indices of refraction from the medium on one side of window 14, window 14, liquid 10, window 16, etc. are different, the second portion 24a will be bent as shown by way of example in the drawing.

Mirrors 40, 42 are positioned to change the direction of second portion 24 at least 180° so that it will pass through window 14 in a direction angularly spaced from and rotated from the direction of travel of the front portion 22 through the windows 40, 42 and the liquid 10.

Beam 24a exiting from second window 16 is directed towards two collimating pin-holes 44, 46 provided in pin-hole device 48 for directing beam 24a travelling in the direction of the arrows thereon towards a second detector 50. Second detector 50 is preferably a small silicon photo-cell which is connected with circuits 52.

Whenever light passes through the two pin holes it is automatically collimated.

When the purity is correct, photocell 50 is energized and the signal sent through circuits 52 is recognized by a device for recording purity (not shown) of the liquid.

When and if any chemical dissolution occurs in the liquid, transmitivity may or may not be detected by the detecting first portion 22, photo-cell 32. However, the second portion 24 of the beam will be affected by a deviation of its path due to the refraction index of the altered liquid that is different, than when the liquid was in pure state. In this case, the collimating pin-holes will shut the light off from the photo-cell. This information through processing will allow to take proper action.

There is no preferred criteria for purities. The apparatus according to the invention is tuned to a given liquid as soon as the purity of the liquid changes; the refraction index changes and the light does not reach the photocell.

While there has been shown and described what is considered to be the presently preferred mode for carrying out the invention, it will be obvious to those skilled in the art that various changes and modifications may be made without departing from the scope of the invention.

What is claimed is:

1. A method for monitoring the purity of a liquid, comprising the steps, of:
    providing a laser beam;
    dividing the laser beam into first and second portions prior to directing the beam through the liquid;
    positioning a pair of windows on opposite sides of the liquid container;
    impinging the first portion of the beam onto a beam expander directed towards one of said windows for passing said first portion through the liquid in a direction to exit through the other side of said windows to thereby survey a relatively large area of the liquid;
    impinging the second portion of the beam onto a mirror arrangement to change the angle of entry of the second portion into the liquid so that it passes through the liquid at an angle different from the direction of travel of the first portion;
    detecting the first portion of the beam after it exits from said second window to detect the amount of the solid particles present in the liquid;
    detecting the second portion of the beam after it exits from the second window; and
    sensing any deviations of the path of the second portion through the liquid as a result of changes in the liquid from its pure state in response to change in refraction effect on said second portion as it passes through the liquid.

2. The method of claim 1, wherein the light is provided by a laser light beam at a wavelength of approximately 0.488 microns.

3. The method of claim 1, wherein the windows are quartz.

4. The method of claim 1, wherein the wavelength of the laser beam is in the range of 0.439 to 0.537 microns.

5. The method of claim 1, including detecting the first portion as it exits from the second window by means of a photocell detector for the detection of contaminants in the liquid.

6. The method of claim 1, including collimating the second portion of the beam before entry through the system of windows and the detection of the beam exit angle as it fails to reach the photocell, this due to a change of refractive index when the liquid has changed its chemical indentity.

7. The method of claim 1, wherein the size of the second portion of the beam prior to impinging through the window is less than 1 mm in diameter.

8. Apparatus for determining the degree of purity of liquid in a container, comprising:
    a pair of spaced windows positioned proximate to the container of liquid;
    a source of laser light in the form of a beam directed towards one of said pair of windows;
    a beam splitter for receiving the laser beam positioned between said source and the container, for splitting said beam into first and second portions;
    a beam expander positioned between said beam splitter and the container and aligned with said beam expander to receive said first portion of the split laser beam and direct said first portion through said windows and through the liquid;
    a beam retractor in line with the second portion for receiving the second portion of the split laser beam;

a pair of angularly related mirrors in line with the second portion of the beam for receiving of the second portion after passing through said beam retractor and directing said second portion towards one window for entry into said container and passage through the liquid to exit from the other of said pair of windows;

detecting means proximate to said other window and aligned with the direction of travel of said first portion after it exits from said other window for detecting said first portion;

second detecting means proximate to said other window and aligned with the direction of travel of said second portion for detecting said second portion after it exits therefrom; and sensing means associated with said second detecting means for sensing any deviations of the path of the second portion through the liquid as a result of changes in the liquid from its pure state in response to change in refraction index on said second portion as it passes through the liquid.

9. Apparatus as claimed in claim 8, wherein said windows are positioned diametrically opposite to each other next to the container.

10. Apparatus as claimed in claim 8, wherein said beam splitter is semi-transparent.

11. Apparatus as claimed in claim 8, wherein said beam expander widens the width of the beam in a direction perpendicular to the direction of beam travel.

12. Apparatus as claimed in claim 8, wherein said mirrors are related and angularly positioned to rotate the second portion at least 180° from the direction of travel of the second portion prior to its impingement onto one of said mirrors.

13. Apparatus as claimed in claim 8, wherein said first detection means includes a photocell.

14. Apparatus as claimed in claim 8, including pin-hole collimating means positioned between said second detecting means and said other window.

15. Apparatus as claimed in claim 14, wherein said pin-hole collimating means includes a pin-hole device provided with two spaced pin-holes for directing the second portion towards said second detecting means.

16. Apparatus as claimed in claim 8, including circuits coupled with said second detecting means for recording purity of the liquid upon energization of said second detection means when the purity is correct.

17. Apparatus as claimed in claim 8, wherein the wavelength of the source is of the order of 0.488 microns.

18. Apparatus as claimed in claim 8, wherein the windows are quartz.

* * * * *